(12) United States Patent
Tanaka et al.

(10) Patent No.: US 8,518,644 B2
(45) Date of Patent: Aug. 27, 2013

(54) METHOD OF JUDGING INFLAMMATORY DISEASE BY USING SINGLE NUCLEOTIDE POLYMORPHISM

(75) Inventors: Toshihiro Tanaka, Tokyo (JP); Yusuke Nakamura, Kanagawa (JP); Yozo Ohnishi, Tokyo (JP); Koichi Ozaki, Tokyo (JP); Aritoshi Iida, Kanagawa (JP); Masatsugu Hori, Osaka (JP)

(73) Assignee: Riken, Saitama (JP)

( * ) Notice: Subject to any disclaimer, the term of this patent is extended or adjusted under 35 U.S.C. 154(b) by 1039 days.

(21) Appl. No.: 11/813,450

(22) PCT Filed: Jul. 6, 2006

(86) PCT No.: PCT/JP2006/300095
§ 371 (c)(1),
(2), (4) Date: Oct. 5, 2009

(87) PCT Pub. No.: WO2006/073183
PCT Pub. Date: Jul. 13, 2006

(65) Prior Publication Data
US 2011/0097711 A1 Apr. 28, 2011

(30) Foreign Application Priority Data
Jan. 7, 2005 (JP) ................................ 2005-003089

(51) Int. Cl.
*C12Q 1/68* (2006.01)
(52) U.S. Cl.
USPC ........................................................ 435/6.11
(58) Field of Classification Search
None
See application file for complete search history.

(56) References Cited

U.S. PATENT DOCUMENTS

| 7,833,706 | B2 * | 11/2010 | Begovich et al. | ............ | 435/6.14 |
| 2003/0092019 | A1 * | 5/2003 | Meyer et al. | ...................... | 435/6 |
| 2005/0260124 | A1 | 11/2005 | Yamada et al. | | |
| 2006/0013817 | A1 | 1/2006 | Sahin et al. | | |

FOREIGN PATENT DOCUMENTS

| EP | 1 536 000 | | 6/2005 |
| WO | 03/076631 | | 9/2003 |
| WO | 2004/001037 | | 12/2003 |
| WO | 2004-015100 | | 2/2004 |
| WO | WO 2004/015100 A1 | * | 2/2004 |
| WO | WO 2004/067779 | * | 8/2004 |

OTHER PUBLICATIONS

NCBI dbSNP record ss3250675. Obtained from http://www.ncbi.nlm.nih.gov/SNP/snp_ss.cgi?subsnp_id=3250674 on Dec. 29, 2011. 2 pages.*
NCBI dbSNP record ss4932618. Obtained from http://www.ncbi.nlm.nih.gov/SNP/snp_ss.cgi?subsnp_id=4932618 on Dec. 29, 2011. 2 pages.*
NCBI dbSNP record ss4935992. Obtained from http://www.ncbi.nlm.nih.gov/SNP/snp_ss.cgi?subsnp_id=4935992 on Dec. 29, 2011. 2 pages.*
Lucentini (2004) The Scientist. Dec. 20, 2004, p. 20.*
Hegele. Arterioscler Thromb Vasc Biol. 2002; 22:1058-1061.*
Haga et al. (J Hum Genet (2002) 47:605-610).*
Yusuf et al. (Lancet 2004; 364: 937-52).*
Nakamura, A. et al., "Ensho Hanno no Seigyo to Proteinase Sogai Inshi" Clinical Immunology 40(5):576-579 (2003).
Hubacek, J. A. et al. Polymorphisms in the Lipopolysaccharide-Binding Protein and Bactericidal/Permeability-Increasing Protein in Patients with Myocardial Infarction, Clin. Chem. Lab. Med. 40(11):1097-1100 (2002).
J Hum Genet. 2002;47(11):605-610.
Database JSNP [online], JSNP ID : IMS-JST060759, <http://snp.ims.u-tokyo.ac.jp/cgi-bin/SnpInfo.cgi?SNP_ID=IMS-JST060759> , Jan. 23, 2002 updated, [retrieved on Jul. 15, 2011].
Japan Office action that issued with respect to patent family member Japanese Patent Application No. 2006-550908, mail date is Jul. 26, 2011, along with a partial English language translation.

* cited by examiner

*Primary Examiner* — Juliet Switzer
(74) *Attorney, Agent, or Firm* — Greenblum & Bernstein, P.L.C.

(57) ABSTRACT

An object of the present invention is to identify a novel single nucleotide polymorphism (SNP) associated with the onset and the advancement of inflammatory diseases such as myocardial infarction. The present invention provides a method for judging an inflammatory disease which comprises detecting at least 1 type of genetic polymorphism existing in at least one gene selected from the group consisting of the LBP-32 gene, the TSBP gene, and the WAP gene.

1 Claim, 4 Drawing Sheets

Fig. 4
a)
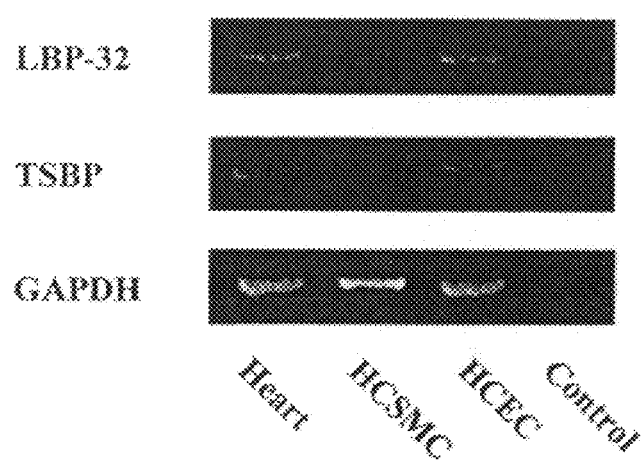
b)
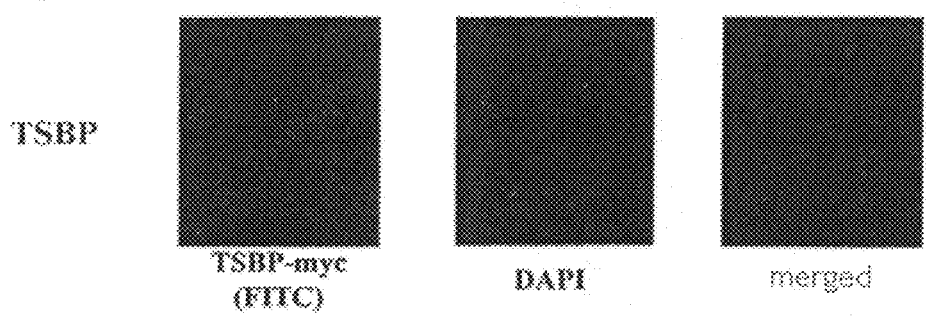
c)
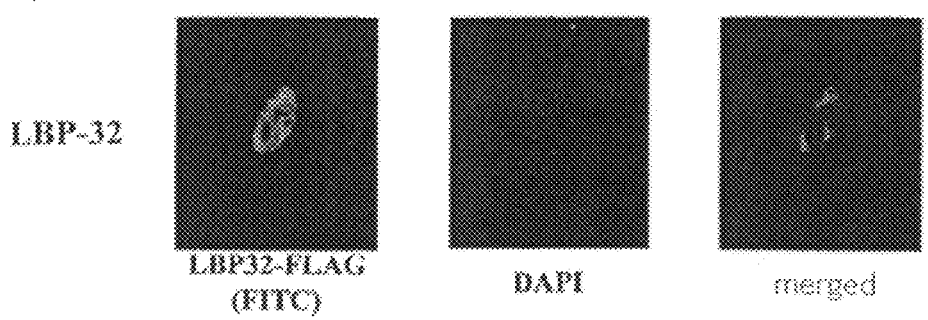

US 8,518,644 B2

METHOD OF JUDGING INFLAMMATORY DISEASE BY USING SINGLE NUCLEOTIDE POLYMORPHISM

TECHNICAL FIELD

The present invention relates to a method for diagnosing inflammatory diseases which comprises detecting genetic polymorphisms existing in a LBP-32 gene, a TSBP gene and a WAP gene, an oligonucleotide to be used in the method, a kit for diagnosing inflammatory diseases which comprises the oligonucleotide, and the use thereof.

BACKGROUND ART

Common genetic variants sometimes exert a strong influence on expression levels and/or functions of the gene products. Such common variants can be associated with susceptibility to diseases and/or pharmacological responsiveness (Dean M, et al., (1996) Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science 273:1856-1862; Risch N, et al., (1996) The future of genetic studies of complex human diseases. Science 273: 1516-1517; and Kruglyak L (1997) The use of a genetic map of biallelic markers in linkage studies. Nat Genet 17: 21-24).

SNPs are most simple and conventional DNA polymorphisms. SNPs are present in every several hundred nucleotides on average throughout the genome and relatively easy to genotype and analyze the data. Recently, it has been hypothesized that common variants may contribute to common diseases and pharmacological traits, so-called "common disease-common variant" hypothesis (Risch N, et al., (1996) The future of genetic studies of complex human diseases. Science 273: 1516-1517). In that point of view, SNPs are useful markers for identifying genes responsible for common diseases (Kruglyak L (1999) Prospects for whole-genome linkage disequilibrium mapping of common disease genes. Nat Genet 22: 139-144).

Myocardial infarction is one of the most common diseases in Japan. Obesity, smoking, diabetes, high blood pressure, and hyperlipidemia are well known risk factors of myocardial infarction. However, family history is an independent risk factor of myocardial infarction in various populations (Andresdottir M B, et al., (2002) Fifteen percent of myocardial infarctions and coronary revascularizations explained by family history unrelated to conventional risk factors, The Reykjavik Cohort Study. Eur Heart J 23: 1637-1638; Piegas LS, et al., AFIRMAR Study Investigators, (2003) Risk factors for myocardial infarction in Brazil, Am Heart J 146: 331-338; and Yarnell J, et al., (2003) Family history, longevity, and risk of coronary heart disease: the PRIME Study, Int J Epidemiol 32: 71-77). Many candidate gene approaches have been used for identifying the susceptiblility gene for myocardial infarction (Topol E J, et al., (2001) Single nucleotide polymorphisms in multiple novel thrombospondin genes may be associated with familial premature myocardial infarction, Circulation 104: 2641-2644; Fumeron F, et al., (2002) Serotonin transporter gene polymorphism and myocardial infarction: Etude Cas-Temoins de l'Infarctus du Myocarde (EC-TIM), Circulation 105: 2943-2945; and Yamada Y, et al., (2002) Prediction of the risk of myocardial infarction from polymorphisms in candidate genes, N Engl J Med 347: 1916-1923). However, there exist almost no reports concerning systemic surveys for identification of genes associated with myocardial infarction.

The present inventors have constructed a large SNP database including SNPs based on over 170,000 or more genes (Haga H, et al., (2002) Gene-based SNP discovery as part of the Japanese Millennium Genome Project: identification of 190,562 genetic variations in the human genome, Single-nucleotide polymorphism, J Hum Genet 47: 605-610). The present inventors have also developed a high-throughput genotyping system by which 450,000 genes were genotyped per day (Ohnishi Y, et al., (2001) A high-throughput SNP typing system for genome-wide association studies, J Hum Genet 46: 471-477).

DISCLOSURE OF THE INVENTION

Object to be Achieved by the Invention

An object to be achieved by the present invention is to identify a novel single nucleotide polymorphism (SNP) associated with the onset and the advancement of inflammatory diseases such as myocardial infarction. Another object to be achieved by the present invention is to provide a method for diagnosing inflammatory diseases such as myocardial infarction or a method for developing a therapeutic agent for inflammatory diseases, through the use of the identified SNPs.

Means for Achieving the Object

As a result of intensive studies to achieve the objects, the present inventors have discovered that single nucleotide polymorphisms (SNPs) existing in a LBP-32 gene, a TSBP gene, and a WAP gene are associated with the onset and the advancement of myocardial infarction. Thus the present inventors have completed the present invention.

Specifically, the present invention provides a method for judging an inflammatory disease which comprises detecting at least 1 type of genetic polymorphism existing in at least one gene selected from the group consisting of the LBP-32 gene, the TSBP gene, and the WAP gene.

Preferably, the present invention provides a method for judging an inflammatory disease which comprises detecting at least 1 type of single nucleotide polymorphism existing in at least one gene selected from the group consisting of the LBP-32 gene, the TSBP gene, and the WAP gene.

Preferably, the present invention provides a method for judging an inflammatory disease which comprises detecting at least one type of single nucleotide polymorphism selected from the group consisting of the following (1) to (3):

(1) a G/A polymorphism at nucleotide 151 in the nucleotide sequence of intron 1 of an LBP-32 gene;
(2) an A/G polymorphism at nucleotide 306 in the nucleotide sequence of exon 25 of a TSBP gene; and
(3) a G/A polymorphism at nucleotide 1264 in the nucleotide sequence of the 3' flanking region of a WAP12 gene.

Preferably, the inflammatory disease is myocardial infarction.

Another aspect of the present invention provides an oligonucleotide which can hybridize to a sequence of at least 10 sequential nucleotides containing at least one site selected from the group consisting of the following (1) to (3) or to a complementary sequence thereof, and is used as a probe in the above method of the present invention:

(1) nucleotide 151 in the nucleotide sequence of intron 1 of an LBP-32 gene;
(2) nucleotide 306 in the nucleotide sequence of exon 25 of a TSBP gene; and (3) nucleotide 1264 in the nucleotide sequence of the 3' flanking region of a WAP12 gene.

Still another aspect of the present invention provides an oligonucleotide which can amplify a sequence of at least 10 sequential nucleotides containing at least one site selected from the group consisting of the following (1) to (3) and/or a complementary sequence thereof and is used as a primer in the above method of the present invention:
(1) nucleotide 151 in the nucleotide sequence of intron 1 of an LBP-32 gene;
(2) nucleotide 306 in the nucleotide sequence of exon 25 of a TSBP gene; and
(3) nucleotide 1264 in the nucleotide sequence of the 3' flanking region of a WAP12 gene.

Preferably, the primer is a forward primer and/or a reverse primer.

Still another aspect of the present invention provides a kit for diagnosing an inflammatory disease which comprises at least one of the above oligonucleotides of the present invention. Preferably, the inflammatory disease is myocardial infarction.

Still another aspect of the present invention provides a method for analyzing the expression status of LBP-32, TSBP, or WAP which comprises detecting at least one type of single nucleotide polymorphism selected from the group consisting of the following (1) to (3):
(1) a G/A polymorphism at nucleotide 151 in the nucleotide sequence of intron 1 of an LBP-32 gene;
(2) an A/G polymorphism at nucleotide 306 in the nucleotide sequence of exon 25 of a TSBP gene; and
(3) a G/A polymorphism at nucleotide 1264 in the nucleotide sequence of the 3' flanking region of a WAP12 gene.

Still another aspect of the present invention provides a method for screening for a therapeutic agent for an inflammatory disease which comprises the steps of analyzing intracellular expression level of an LBP-32 gene, a TSBP gene, or a WAP gene in the presence of a candidate substance and selecting a substance that alters the expression level.

PREFERRED EMBODIMENTS FOR CARRYING OUT THE INVENTION

In the present invention, single nucleotide polymorphisms (SNPs) within an LBP-32 gene, a TSBP gene, and a WAP gene were identified, genotyping was performed for a myocardial infarction patient group and a control group, and then association analysis was conducted. As a result, it was discovered that the novel SNP genotypes differed statistically significantly between the myocardial infarction patient group and the control group.

As described above, it was determined in the present invention that SNP within the LBP-32 gene, the TSBP gene, or the WAP gene was associated with diseases such as myocardial infarction. Accordingly, the use of such SNPs within the LBP-32 gene, the TSBP gene, or the WAP gene which were identified in the present invention makes it possible to develop a novel method for diagnosing, a novel method for preventing, or a novel therapeutic agent for inflammatory diseases such as myocardial infarction. Hereinafter, the embodiments of the present invention will be further specifically described.

[1] Method for Judging Inflammatory Diseases

The method of the present invention is a method for judging the occurrence or the non-occurrence of the onset of an inflammatory disease or the possible onset of an inflammatory disease by the detection of a genetic polymorphism, particularly a single nucleotide polymorphism (SNP) existing in the LBP-32 gene, the TSBP gene, or the WAP gene which is associated with the inflammatory disease.

In the present invention, "detecting at least one type of genetic polymorphism (e.g., single nucleotide polymorphism) existing in at least one gene selected from the group consisting of an LBP-32 gene, a TSBP gene, and a WAP gene" refers to both (i) direct detection of such genetic polymorphism (referred to as a polymorphism on the gene side) and (ii) detection of such genetic polymorphism (referred to as a polymorphism on the complementary side) existing on the side of a sequence complementary to the above gene, followed by presumption of the polymorphism on the gene side based on the detection result. However, since nucleotides on the gene side are not always completely in complementary relationships with nucleotides on the complementary sequence side, direct detection of a polymorphism on the gene side is preferable.

Preferable specific examples of genetic polymorphisms existing in the LBP-32 gene, the TSBP gene, and the WAP gene include:
(1) a G/A polymorphism at nucleotide 151 in the nucleotide sequence of intron 1 (the nucleotide sequence shown in SEQ ID NO: 1) of the LBP-32 gene;
(2) an A/G polymorphism at nucleotide 306 in the nucleotide sequence of exon 25 (the nucleotide sequence shown in SEQ ID NO: 2) of the TSBP gene; and
(3) a G/A polymorphism at nucleotide 1264 in the nucleotide sequence of the 3' flanking region (the nucleotide sequence shown in SEQ ID NO: 3) of the WAP12 gene.

For example, as shown in Table 2 below, when nucleotide 151 in the nucleotide sequence of intron 1 of the LBP-32 gene is A, it can be judged that an inflammatory disease is being developed or will be likely to be developed. Similarly, when nucleotide 306 in the nucleotide sequence of exon 25 of the TSBP gene is G, it can be judged that an inflammatory disease is being developed or will be likely to be developed. Furthermore, when nucleotide 1264 in the nucleotide sequence of the 3' flanking region of the WAP12 gene is A, it can be judged that an inflammatory disease is being developed or will be likely to be developed.

In contrast, when nucleotide 151 in the nucleotide sequence of intron 1 of the LBP-32 gene is G, when nucleotide 306 in the nucleotide sequence of exon 25 of the TSBP gene is A, and when nucleotide 1264 in the nucleotide sequence of the 3' flanking region of the WAP12 gene is G, it can be judged that an inflammatory disease will be unlikely to be developed.

In the description, "judgment" of a disease means to judge the occurrence or the non-occurrence of the onset of a disease, to judge the possibility of the onset of a disease (prediction of affection risk), to elucidate genetic factors of a disease, and the like.

Furthermore, "judgment" of a disease can also be performed based on the results obtained by the above method for detecting single nucleotide polymorphisms and the results obtained by other forms of polymorphism analysis (VNTR or RFLP) and/or other test results, if desired.

Moreover, in the description, "inflammatory disease" is not particularly limited, as long as it is a disease which shows induction of cell adhesion factors or cytokines which are known to be associated with pathological inflammatory conditions. Examples of such inflammatory disease include chronic rheumatoid arthritis, systemic lupus erythematosus, inflammatory enteritis, various allergic reactions, bacterial shock, and arteriosclerotic diseases such as myocardial infarction or apoplectic stroke. In particular, such inflammatory disease is myocardial infarction.

(Detection Subjects)

A subject of genetic polymorphism detection is preferably genomic DNA. Depending on circumstances (specifically, when the sequence of a polymorphism site or the sequence of its neighboring region is identical to or completely complementary to the genome), cDNA or mRNA can also be used. Furthermore, examples of samples from which the above subjects are collected include: any biological samples such as body fluids (e.g., blood, bone marrow aspirate, seminal fluid, abdominal fluid, and urine); cells of tissues such as those in the liver; and hair such as body hair. Genomic DNA and the like can be extracted, purified and then prepared from these samples according to conventional methods.

(Amplification)

Upon genetic polymorphism detection, first a portion containing a genetic polymorphism is amplified. Amplification is performed by the PCR method, for example. Amplification may also be performed by another known amplification method such as an NASBA method, an LCR method, an SDA method, or a LAMP method.

Primers are selected so that a sequence of at least 10 sequential nucleotides, preferably 10 to 100 sequential nucleotides, and more preferably 10 to 50 sequential nucleotides containing the aforementioned single nucleotide polymorphism sites of the present invention and/or the complementary sequences thereof is amplified.

A primer may also contain 1 or more instances of substitution, deletion, and/or addition in its sequence, as long as it is capable of functioning as a primer for amplifying a sequence of a predetermined number of nucleotides containing the above single nucleotide polymorphism site.

Primers to be used for amplification may also be selected so that either a forward primer or a reverse primer hybridizes to a single nucleotide polymorphism site. In this case, amplification takes place only when a sample is of a single allele genotype. Primers can be labeled with a fluorescent substance, a radioactive substance, or the like, if necessary.

(Detection of Genetic Polymorphisms)

Genetic polymorphisms can be detected by hybridization with a probe specific to a single allele genotype. A probe may be labeled with a fluorescent substance, a radioactive substance, or the like, if necessary, by adequate means. A probe to be used herein is not particularly limited, as long as it contains the above single nucleotide polymorphism site, can hybridize to a test sample, and imparts specificity at a detectable level under detection conditions to be employed. As such probe, an oligonucleotide capable of hybridizing to a sequence of at least 10 sequential nucleotides, preferably 10 to 100 sequential nucleotides, and more preferably 10 to 50 sequential nucleotides containing the above single nucleotide polymorphism site or a sequence complementary thereto can be used, for example. For example, an invader method or a TaqMan-PCR method can be employed. Moreover, it is preferable to select an oligonucleotide, so that a single nucleotide polymorphism site is present at almost the center of the probe. Such oligonucleotide may contain one or more instances of substitution, deletion, and/or addition, as long as it is capable of functioning as a probe, and specifically, as long as it hybridizes under conditions such that it hybridizes to a sequence of a target allele genotype but does not hybridize to sequences of other allele genotypes. Furthermore, another example of a probe to be used herein is a probe that satisfies the above probe conditions, such as a single-strand probe (padlock probe) to be used in amplification performed by an RCA (rolling circle amplification) method. Specifically, such probe anneals to genomic DNA to form a cyclic form, and thus it satisfies the above probe conditions.

Hybridization conditions to be employed in the present invention are conditions sufficient for distinguishing allele genotypes. For example, such conditions are conditions such as stringent conditions, in which hybridization takes place when a sample is of one allele genotype but hybridization does not take place when a sample is of another allele genotype. Here, "stringent conditions" are conditions described in Molecular Cloning A Laboratory Manual, $2^{nd}$ ed., (Sambrook et al., 1989), for example. Specifically, such conditions involve overnight incubation at 65° C. with a probe in a solution containing 6×SSC (1×SSC composition: 0.15 M NaCl, 0.015 M sodium citrate, and pH 7.0), 0.5% SDS, 5×Denhardt, and 100 mg/ml herring sperm DNA, for example.

One end of a probe may be immobilized on a substrate and then the substrate can also be used as a DNA chip. On such a DNA chip in this case, only probes that correspond to a single allele genotype may be immobilized, or probes that correspond to both allele genotypes may be immobilized.

Genetic polymorphisms can also be detected by a restriction fragment length polymorphism (RFLP) analysis method. With this method, a sample nucleic acid is digested with a restriction enzyme (whether or not cleavage with the restriction enzyme takes place depends on the genotype of a single nucleotide polymorphism site) and then the size of a digested product (fragment) is examined. Thus whether or not the sample nucleic acid is cleaved with the restriction enzyme is determined, so that the polymorphism of the sample is analyzed.

Genetic polymorphisms can also be detected by direct sequencing of amplified products (direct sequencing method). Sequencing can be performed by a known method such as a dideoxy method or a Maxam-Gilbert method.

For genetic polymorphism detection, denaturing gradient gel electrophoresis (DGGE), single strand conformation polymorphism (SSCP) analysis, allele-specific PCR, a hybridization method that involves an allele-specific oligonucleotide (ASO), chemical cleavage of mismatches (CCM), an HET (heteroduplex method) method, a PEX (primer extension) method, an RCA (rolling circle amplification) method, or the like can also be employed.

[2] Kit for Diagnosing Inflammatory Diseases

A kit for diagnosing inflammatory diseases including the above oligonulceotide to be used as a primer or a probe can be provided. The kit may also include restriction enzymes, polymerase, nucleoside triphosphate, labels, buffers, and the like, which are used for the above method for analyzing genetic polymorphisms.

[3] Method for Analyzing the Expression Status of LBP-32, TSBP, and WAP

According to the present invention, the expression status of LBP-32, TSBP, or WAP can also be analyzed by detection of the above single nucleotide polymorphisms.

For example, when nucleotide 151 is A in the case of a G/A polymorphism at nucleotide 151 in the nucleotide sequence of intron 1 of the LBP-32 gene, the expression level of LBP-32 can be judged to be low; and when the nucleotide 151 is G, the expression level of LBP-32 can be judged to be high.

[4] Method for Screening for a Therapeutic Agent for Inflammatory Diseases

According to the present invention, a therapeutic agent for inflammatory diseases can be screened by analyzing the intracellular expression level of the LBP-32 gene, the TSBP gene, or the WAP gene in the presence of candidate substances and then selecting a substance that alters the expression level. For example, the intracellular expression level of the LBP-32 gene, the TSBP gene, or the WAP gene is analyzed in the presence of candidate substances and then a substance that increases or decreases such expression level can be selected. Particularly preferably, a substance that increases the expression level can be selected.

An example of the above screening that can be conducted herein involves the steps of: causing cells to come into contact with candidate substances; analyzing the intracellular expression level of the LBP-32 gene, the TSBP gene, or the WAP gene; and selecting a candidate substance that alters the expression level of the relevant gene through comparison with expression level under conditions in which the candidate substance is absent, as a therapeutic agent for inflammatory diseases.

As such candidate substance, any substance can be used, and candidate substance types are not particularly limited. The candidate substance may be an individual low-molecular-weight synthetic compound or a compound existing in an extract from a natural product. Alternatively, the candidate substance may be a member of a compound library, a phage display library, or a combinatorial library. The candidate substance is preferably a low-molecular-weight compound and is preferably a member of a low-molecular-weight compound library. Construction of a compound library is known by persons skilled in the art. Moreover, a commercial compound library can also be used.

[5] Method for Determining the Transcriptional Activity of the LBP-32 Gene, the TSBP Gene, or the WAP Gene According to the present invention, the transcriptional activity of the LBP-32 gene, the TSBP gene, or the WAP gene can be determined by introducing a fragment of the LBP-32 gene, the TSBP gene, or the WAP gene containing the above single nucleotide polymorphism into cells, culturing the cells, and then analyzing the expression of the gene.

According to a preferred embodiment of the present invention, the expression of the gene is analyzed by introducing a transcription unit wherein a reporter gene has been bound downstream of a fragment of the LBP-32 gene, the TSBP gene, or the WAP gene into cells, culturing the cells, and then determining the reporter activity.

For example, when a single nucleotide polymorphism is present in the promoter site, cells in which a system having a reporter gene inserted downstream of a gene containing the single nucleotide polymorphism has been introduced are cultured, and then the reporter activity is determined. Hence, a difference in transcription efficiency due to the single nucleotide polymorphism can be measured.

Reporter genes to be used herein are genes of luciferase, chloramphenicol, acetyltransferase, galactosidase, and the like.

[6] Method for Screening for a Substance Inhibiting or Promoting the Transcriptional Activity of the LBP-32 Gene, the TSBP Gene, or the WAP Gene According to the present invention, a substance inhibiting or promoting the transcriptional activity of the LBP-32 gene, the TSBP gene, or the WAP gene can be screened by introducing a fragment of the LBP-32 gene, the TSBP gene, or the WAP gene containing the above single nucleotide polymorphism into cells, culturing the cells in the presence of candidate substances inhibiting or promoting the transcriptional activity of the LBP-32 gene, the TSBP gene, or the WAP gene, and then analyzing the expression of the gene.

According to a preferred embodiment of the present invention, the expression of the gene is analyzed by introducing a transcription unit wherein a reporter gene has been bound downstream of a fragment of the LBP-32 gene, the TSBP gene, or the WAP gene into cells, culturing the cells, and then determining the reporter activity.

For example, a system having a reporter gene inserted downstream of a gene having a single nucleotide polymorphism and exerting a significantly high expression level of the LBP-32 gene, the TSBP gene, or the WAP gene is introduced into cells. The cells are cultured in both the presence and the absence of a candidate substance. If lower reporter activity is determined when culture is carried out in the presence of the candidate substance, the candidate substance can be selected as a substance that inhibits the transcriptional activity of the LBP-32 gene, the TSBP gene, or the WAP gene.

As reporter genes to be used herein, the genes listed above are used.

As such candidate substance, any substance can be used, and candidate substance types are not particularly limited. The candidate substance may be an individual low-molecular-weight synthetic compound or a compound existing in an extract from a natural product. Alternatively, the candidate substance may be a member of a compound library, a phage display library, or a combinatorial library. The candidate substance is preferably a low-molecular-weight compound and is preferably a member of a low-molecular-weight compound library. Construction of a compound library is known by persons skilled in the art. Moreover, a commercial compound library can also be used.

Substances that inhibit or promote the transcriptional activity of the LBP-32 gene, the TSBP gene, or the WAP gene, which are obtained by the above screening method, are also encompassed within the scope of the present invention. Such substances inhibiting or promoting the transcriptional activity of the LBP-32 gene, the TSBP gene, or the WAP gene are useful as candidate substances to be used as various drugs such as therapeutic agents for myocardial infarction, anti-inflammatory agents, and immunosuppressant agents.

[7] Method for Screening for a Transcriptional Control Factor of the LBP-32 Gene, the TSBP Gene, or the WAP Gene According to the present invention, a transcriptional control factor of the LBP-32 gene, the TSBP gene, or the WAP gene can also be screened by causing a gene fragment containing the above single nucleotide polymorphism to come into contact with a sample assumed to contain a transcriptional control factor of the LBP-32 gene, the TSBP gene, or the WAP gene and then detecting the binding of the fragment with the transcriptional control factor. Binding of such gene fragment containing the above single nucleotide polymorphism with a substance assumed to contain a transcriptional control factor of the LBP-32 gene, the TSBP gene, or the WAP gene can be detected by a gel shift method (electrophoretic mobility shift assay (EMSA)), a DNase I footprint method, or the like. In particular, the gel shift method is preferred. The gel shift method involves mixing a $^{32}$P-labeled gene fragment with a transcriptional control factor and then subjecting the mixture to gel electrophoresis. This is because when a protein (transcriptional control factor) binds, the molecular size will increase and DNA mobility in electrophoresis will decrease in the case of the gel shift method. It can be noted that DNA with such factor bound thereto moves slowly, when the position of the DNA is observed by autoradiography. Thus, such DNA is detected as a band that shifts behind the general band.

The present invention will be further specifically described in detail by referring to the following examples. However, the present invention is not limited by these examples.

EXAMPLE

(A) Materials and Methods

(1) Subjects

Japanese myocardial infarction patients were used. The diagnostic of definite myocardial infarction requires two of the following three criteria: (i) a clinical history of central chest pressure, pain, or tightness lasting for 30 minutes or more, (ii) ST-segment elevation of 0.1 mV or more based on at least one standard or in two precordial leads, and (iii) a rise in serum creatine kinase concentration twice or more the normal laboratory value. A control group consisted of healthy Japanese subjects. All subjects (patients) agreed to participate in this experiment.

(2) SNP Genotyping

For a large-scale association analysis, the present inventors used their own SNP database (Haga H, et al., (2002) Gene-based SNP discovery as part of the Japanese Millennium Genome Project: Identification of 190,562 genetic variations in the human genome. Single-nucleotide polymorphism. J Hum Genet 47: 605-610) and carried out screening for SNPs as in the previous report (Ohnishi Y, et al., (2001) A high-throughput SNP typing system for genome-wide association studies. J Hum Genet 46: 471-477). To construct an SNP map in a critical region, a reference sequence was generated by assembling AC010969.11 for LBP-32. Z84814.1, AL034394.2, AL035445.4, AF044083.1, and U89335.1 were used for TSBP. AL031663.2, AL121778.12, AL031671.12, AL109656.10, and AL050348.21 were used for a WAP region. Next, SNPs were deposited in the reference sequence. To evaluate intense linkage disequilibrium, the SNP sites of 190 myocardial infarction patients and 190 control subjects were genotyped.

(3) Identification of SNP

To identify all gene-based variations in the critical region, all genes known to be located in the critical region were screened. Protocols for PCR primer design, PCR experiments, DNA extraction, DNA sequencing, and SNP identification were as in the previous report (Iida et al. 2001). SNPs in the critical region were genotyped as in the previous report by direct sequencing of PCR products with the use of invader assay or a capillary sequencer (ABI3700, Applied Biosystems, CA) (Iida A, et al., (2001) Catalog of 258 single-nucleotide polymorphisms (SNPs) in genes encoding three organic anion transporters, three organic anion-transporting polypeptides, and three NADH: Ubiquinone oxidoreductase flavoproteins. J Hum Genet 46: 668-683; and Ohnishi Y, et al., (2001) A high-throughput SNP typing system for genome-wide association studies. J Hum Genet 46: 471-477).

(4) Haplotype Structure Analysis

Haplotype phasing was estimated based on an EM-algorithm (Excoffier L, et al., (1995) Maximum-likelihood estimation of molecular haplotype frequencies in a diploid population, Mol Biol Evol 12: 921-927). A haplotype block was constructed as in the previous report excluding the following improvement (Daly M J, et al., (2001) High-resolution haplotype structure in the human genome, Nat Genet 29: 229-232). First, to make the next analysis simple, neighboring SNPs absolutely linking to a single representative SNP were clustered. Next, a constraint such that a common haplotype set represented by $maxN+1,2^{0.5N}$ (wherein N denotes the number of SNPs in the block) accounts for 90% or more of a population was imposed. To eliminate vagueness, samples for which no SNP sites could be genotyped as a result of the calculation of haplotype frequencies were excluded.

(5) Statistical Analysis

Statistical analyses for association study, Hardy-Weinberg equilibrium, and calculation of linkage disequilibrium coefficients (D') were carried out as in the previous reports (Yamada R, et al., (2001) Association between a single-nucleotide polymorphism in the promoter of the human interleukin-3 gene and rheumatoid arthritis in Japanese patients, and maximum-likelihood estimation of combinatorial effect that two genetic loci have on susceptibility to the disease. Am J Hum Genet 68: 674-685).

(6) Luciferase Activity

A DNA fragment corresponding to intron 1 (+5 to +350) of LBP-32 was amplified by PCR using Hind III and Nco I sequences and using genomic DNA as a template. The resultant was cloned into Hind III and Nco I sites of a pGL3-promoter vector in the 5'-3' direction. HeLa cells were grown in DMEM medium supplemented with 10% fetal bovine serum. Subsequently, cells ($3 \times 10^5$) were transfected with 0.5 µg of a wild-type construct or a mutant construct and 0.5 µg of a pRL-TK vector (an internal control for transfection efficiency) using an FuGene transfection reagent (Roche, Ind.). 24 hours later, cells were harvested and then luciferase activity was determined using a Dual-Luciferase Reporter Assay System (Promega, Wis.).

(7) Gel-Shift Assay

A nuclear extract was prepared from HeLa cells as described in the previous report (Andrews and Faller 1991) and then incubated with $^{32}$P-labeled oligonucleotides (28 bp each) 5'-TCCACGCCGCCACGGCCTTTGCCCCTTA-3' (allele G) (SEQ ID NO: 4) and 5'-TCCACGCCGCCAC-GACCTTTGCCCCTTA-3' (allele A) (SEQ ID NO: 5). For competition studies, an extracted nucleus was preincubated with unlabelled oligonucleotides (100-fold excess) before the addition of $^{32}$P-labeled oligonucleotides. The protein-DNA complexes were separated on non-denaturing 8% polyacrylamide gel in 0.5×Tris-Borate-EDTA buffers. Signals were detected by autoradiography.

(8) Expression Analysis using RT-PCR

Total RNA was isolated from HCASMC (BioWhittaker) and HCAEC (BioWhittaker) using a TRIZOL reagent (GibcoBRL). Single-strand cDNA was prepared using an oligo dT primer and Superscript II reverse transcriptase (Invitrogen) from the total RNAs of HCASMC and HCAEC and polyA RNA (Clontech) of a human heart tissue. PCR amplification was performed using the cDNAs as templates, 5'-ACTTTG-GCTGTCATCCTGAC-3' (SEQ ID NO: 6) and 5'-CTTGAT-AGGTCCTGTAGCTC-3' (SEQ ID NO: 7) (for TSBP), 5'-AGCGCGATGACACAGGAGTA-3' (SEQ ID NO: 8) and 5'-CGTTGCTATGGAGACAGTGA-3' (SEQ ID NO: 9) (for LBP-32), or 5'-TGGTATCGTGGAAGGACTCAT-3' (SEQ ID NO: 10) and 5'-GTGGGTGTCGCTGTTGAAGTC-3' (SEQ ID NO: 11) (for GAPDH as internal reference) as primers.

(9) Construction of Expression Vector

Human full-length TSBP and LBP-32 cDNAs were prepared by RT-PCR using the following PCR primer sets:

```
                                          (SEQ ID NO: 12)
5'-ATAGCGGCCGCAATGACAGTCTTGGAAATAAC-3'
and (SEQ ID NO: 13)
5'-AGACTCGAGTTACTCTTCCACTTTTTTGTTGTAC-3';
and (SEQ ID NO: 14)
5'-GAGGCGGCCGCGATGACACAGGAGTACGACAAC-3'
and
```

-continued (SEQ ID NO: 15)
5'-AGAGTCGACGATCTCCGTCAGGGTGAGC-3'.

pTSBP-myc was constructed by inserting the TSBP cDNA digested with Not I-Xho I into pCMV-myc (Clontech, Palo Alto, Calif.). pLBP32-Flag was constructed by inserting a LBP-32 cDNA digested with Not I-Sal I into pFLAG-CMV5a (Sigma).

(10) Immunofluorescence Analysis

HCASMC cells ($5\times10^5$) were transfected with 5 μg of pTSBP-myc or pLBP32-Flag by Human AoSMC Nucleofector Kit (amaxa biosystems) and then seeded on collagen-coated glass slide. After 24 hours of culture, cells were fixed and then treated with antibodies. Nuclei were stained with DAPI (Sigma).

(B) Results (1) SNP Association Studies

First, the genotype frequency in 94 myocardial infarction patients was compared with the genotype frequency in 658 healthy subjects regarding 65,671 SNPs. Subsequently, genotyping was further performed for SNPs with P values of less than 0.01 in a larger replication panel. As the results of further genotyping, four SNP sites including the LTA site were found to show significant association (p<0.0001) with myocardial infarction, as shown in Table 1. The other three sites were located in the LBP-32 gene on chromosome 2p25.1, the TSBP gene on chromosome 6p21, and the WAP12 gene on chromosome 20q13, respectively.

TABLE 1

| P value | Dominant model | Recessive model |
|---|---|---|
| >=0.01 | 1,299 | 1,307 |
| <0.01 | 27 | 18 |
| <0.001 | 6 | 5 |
| <0.0001 | 1 | 3 |
| total | 1,333 | 1,333 |

TABLE 3

(SEQ ID NOS 16-18, respectively in order of appearance)

| Name | Sequence |
|---|---|
| TSBP exon25 306A > G | 5'-TAAAAATCAGTGAGATGAGT[A/G]TACCACAAGGACAGGGAGCC-3' |
| LBP-32 Intron1 + 151G > A | 5'-GTCCACTCCACGCCGCCACG[G/A]CCTTTGCCCCTTAGCCCTGC-3' |
| WAP12 3'flanking + 1264G > A | 5'-AGACATCATCAGCAGTAGGT[G/A]GGCTATAAGGGCATGGTCTC-3' |

(2) Linkage Disequilibrium Analysis

To estimate the extension of intense linkage disequilibrium (LD) in these critical regions, the above SNPs in 95 myocardial infarction patients and 95 control subjects were genotyped.

LBP-32 Gene Region:

Eleven SNPs spanning 157 kb on chromosome 2p25.1 including TAF1B and LBP-32 were genotyped. An extended block of intense linkage disequilibrium including LBP-32 is shown in FIG. 1a.

TSBP Region:

Twenty two SNPs spanning 250 kb on chromosome 6p21 including BTNL2, TSBP, and NOTCH4 were genotyped. The allele frequency of these SNPs was 30% or more. The D' value of each SNP pair was plotted and labeled (FIG. 1a). Significant SNPs were located in one block of intense linkage disequilibrium and D' was decreased upstream and downstream of TSBP (FIG. 2a).

WAP Region:

15 SNPs spanning 376 kb on chromosome 20q13 including WAP7-13 and TNNC2 were genotyped. An extended block of intense linkage disequilibrium including WAP8-13 is shown in FIG. 3a.

(3) High-Density SNP Mapping and Haplotype Block Analysis

TABLE 2

| Genotype | Myocardal infarction | Control | Chi square (p value) | Odds ratio (95% c.i.) |
|---|---|---|---|---|
| TSBP exon25 306A > G | | | | |
| AA | 1077 (58.4%) | 1057 (65.0%) | AA vs. GG+AG | 1.32 (1.15-1.52) |
| AG | 661 (35.8%) | 496 (30.5%) | 16.1 (0.000062) | |
| GG | 107 (5.8%) | 73 (4.5%) | | |
| LBP-32 intron1 + 151G > A | | | | |
| GG | 1475 (79.3%) | 1247 (77.3%) | AA vs. GG+GA | 3.71 (1.85-7.41) |
| GA | 342 (18.4%) | 357 (22.1%) | 15.7 (0.000072) | |
| AA | 42 (2.3%) | 10 (0.6%) | | |
| WAP12 3'flanking + 1264G > A | | | | |
| GG | 775 (41.6%) | 767 (47.1%) | AA vs. GG+GA | 1.60 (1.29-1.99) |
| GA | 837 (45.0%) | 717 (44.0%) | 18.2 (0.000019) | |
| AA | 250 (13.4%) | 144 (8.8%) | | |

To identify all gene-based variations in LBP-32, approximately 52 kb including all the exons of LBP-32 was screened. A total of 40 polymorphisms in this region were identified and then genotyped for 190 myocardial infarction patients and 190 healthy subjects. No significant association was observed as a result of this genotyping except for LBP-32 intron 1+151G>A.

For TSBP, approximately 80 kb including all the exons were screened. A total of 216 polymorphisms in this region were identified. To estimate haplotype blocks, the above-found SNPs with the allele frequency of 20% or more were genotyped for 95 myocardial infarction patients and 95 healthy subjects. As a result of this genotyping, a haplotype block containing TSBP exon 25 306A>G for which significant association had been observed was discovered (FIG. 2b).

For the WAP gene region, WAP7-13 and TNNC2 were screened. A total of 54 polymorphisms were identified in this region and then genotyped for 95 myocardial infarction patients and 95 healthy subjects. As a result of this genotyping, a haplotype block containing SNPs in the 3' flanking region of the WAP12 gene was discovered. The haplotype block was composed of 18 SNPs spanning over approximately 100 kb. These 18 SNPs were further genotyped for other 475 myocardial infarction patients and other 475 healthy subjects. As a result of this genotyping, the most significant association was observed in a plurality of SNPs containing the 3' flanking region+1264G>A of the WAP12 gene (FIG. 3b).

(4) Expression and Localization of the TSBP Gene and the LBP-32 Gene in Human Heart Gene expression of TSBP and LBP-32 were analyzed by RT-PCR. A TSBP transcript was detected in coronary artery endothelial cells (HCAEC) and coronary artery smooth muscle cells (HCASMC) (FIG. 4a). An LBP-32 transcript was also detected in human heart tissues and HACEC (FIG. 4a).

To examine the cellular localization of TSBP and LBP-32, HACSMC was transfected with Myc-tagged TSBP or Flag-tagged LBP-32. As a result, TSBP was found to be localized in the cytoplasm and LBP-32 was found to be localized in the nucleus (FIGS. 4b and c).

(5) Binding of Nuclear Factors to SNP Sites

To examine whether any nuclear factors bind to the SNP (intron 1+151G>A) in LBP-32, gel-shift assay was performed using oligonucleotides containing SNP sites. A marked shift band was observed only when oligonucleotides containing allele A had been used (FIG. 1b).

(6) Transcriptional Regulatory Activity Affected by SNP

To determine whether the SNP (intron 1+151G>A) in LBP-32 would affect its expression level, two plasmids were constructed using a genomic DNA fragment corresponding to each allele upstream of a luciferase gene transcriptional unit. The relative luciferase activity of a clone corresponding to allele A was about a half of that of a clone corresponding to allele G (FIG. 1c).

(C) Discussion

Large-scale association studies were conducted for myocardial infarction using 92,788 SNPs. 65,671 SNPs (70.7%) were genotyped for 94 myocardial infarction patients. These SNPs covered 13,738 genes. This means that our screening accounted for approximately 43% of all estimated genes. Over 96% of screened SNPs (in the primary screening) for which a p value of less than 0.01 had been achieved failed to keep a significant association with another set of samples. This result indicates that association studies involving small numbers of samples are meaningless for common diseases.

As a result of the large-scale association study of this Example, significant association with increased risk for myocardial infarction was confirmed at 4 SNPs. Of these 4 SNPs, one SNP is located on LTA as in the previous report (Ozaki K, et al., (2002) Functional SNPs in the lymphotoxin-alpha gene that are associated with susceptibility to myocardial infarction, Nat Genet 32: 650-654). The other two SNPs were located on TSBP and LBP-32. The last SNP was located on the WAP locus on chromosome 20q13.

LBP-32 was cloned as a protein which binds to a promoter region of cytochrome P450scc (Huang N, et al., (2000) Cloning of factors related to HIV-inducible LBP proteins that regulate steroidogenic factor-1-independent human placental transcription of the cholesterol side-chain cleavage enzyme, P450scc. J Biol Chem 275: 2852-2858). This is identical to human p70 MGR and is 94% identical to mouse MGR (Wilanowski T, et al., (2002) A highly conserved novel family of mammalian developmental transcription factors related to Drosophila grainyhead, Mech Dev 114: 37-50). Wilanowski et al. have reported that p70 MGR binds to the promoter regions of Drosophila dopa decarboxylase, Drosophila PCNA, and human En-1. As a result of an overexpression study using Flag-tagged LBP-32, LBP-32 was found to be localized in the nucleus in a manner similar to the case of mouse MGR. Substitution of LBP-32 intron 1+151G>A results in a change in the binding motif of a nuclear factor. Specifically, allele G has no motifs, whereas allele A has a COUP/HNF-4 heterodimer binding motif. As a result of luciferase assay, it was suggested that a minor allele of LBP-32 intron 1+151G>A may suppress the expression level of LBP-32, so that the expression levels of downstream genes may be modulated. P450scc is also referred to as estrogen synthetase. Because estrogen plays an important role in coronary events, modulation of the expression level of P450scc may relate to the onset of myocardial infarction. The mechanism for affecting expression levels may be binding of nuclear factor(s) to minor allele A (FIG. 1b).

TSBP has been identified for the first time from testis cDNA (Liang Z G, et al., (1994) Human testis cDNAs identified by sera from infertile patients: a molecular biological approach to immunocontraceptive development, Reprod Fertil Dev 6: 297-305). However, TSBP cDNA was detected in human heart tissues and HCAEC (FIG. 3). In HCASMC, TSBP is localized in the cytoplasm. A significant SNP in TSBP (exon 25 306A>G) is localized in a coding region and results in amino acid substitution (I306V). TSBP was mapped to 6p21 where LTA was also located. Two genes were located at intervals of approximately 700 kb and were located in different linkage disequilibrium blocks. Moreover, D' between the critical SNP of TSBP and that of LTA was 0.4. This indicates that significant association between TSBP and myocardial infarction is independent of LTA.

A locus on chromosome 20q13 contains many genes encoding proteins having homology with whey acidic protein (WAP). Potential functions of WAPs can relate to host defense against microorganims (Clauss A, et al., (2002) A locus on human chromosome 20 contains several genes expressing protease inhibitor domains with homology to whey acidic protein, Biochem J 368: 233-242). The linkage disequilibrium block containing SNPs at which significant association had been observed extended to approximately 300 kb. A target region was limited to 100 kb for haplotype block analysis. Four WAP genes are present within the limited target region. Since these genes contain overlapping regions, it is difficult to focus on the gene associated with myocardial infarction.

As described in the above Example, two candidate genes and one candidate locus susceptible for the onset of myocardial infarction were identified by a large-scale association study.

Industrial Applicability

According to the present invention, novel single nucleotide polymorphisms (SNPs) associated with the onset and the advancement of inflammatory diseases such as myocardial infarction have been newly identified. The use of these SNPs identified according to the present invention enables the provision of a method for diagnosing inflammatory diseases such as myocardial infarction or a method for developing a therapeutic agent for inflammatory diseases.

BRIEF DESCRIPTION OF THE DRAWINGS

FIG. 1(a) shows pairwise linkage disequilibrium between SNPs, as measured by D' in the genomic region that includes TAF1B and LBP-32. 11 common SNPs were genotyped. Allelic frequencies of these SNPs were 30% or more. LBP-32 was localized in one linkage disequilibrium block. Dark black areas represent intense linkage disequilibrium, while white areas represent D'<0.5. FIG. 1(b) shows the binding of unknown nuclear factor(s) to an LBP-32 intron 1. An arrow indicates the band that shows the binding of nuclear factor(s) to the allele A, not to the allele G. FIG. 1(c) shows the effect of SNP in an LBP-32 intron on relative luciferase activity. Relative luciferase activity due to allele A was significantly lower than that in the case of allele G. *P=0.0001 for the comparison between allele G and allele A using a Student t-test.

FIG. 2(a) shows pair wise linkage disequilibrium between SNPs, as measured by D' in the genomic region that include BTNL2, TSBP, and NOTCH4. 22 common SNPs were genotyped. Allelic frequencies of these SNPs were 30% or more. The TSBP gene was localized in one linkage disequilibrium block. Dark black areas represent intense linkage disequilibrium, while white areas represent D'<0.5. FIG. 2(b) shows haplotype blocks and P-value distribution. The haplotype blocks contained 11 common SNPs including exon 25 306A>G. The most significant association was observed at the last exon of TSBP (exon 25 306A>G) (indicated with an arrow). FIG. 2(b) discloses SEQ ID NOS 19-21, respectively, in order of appearance.

FIG. 3(a) shows pairwise linkage disequilibrium between SNPs, as measured by D' in the genomic region that includes WAP7-13 and TNNC2. 15 common SNPs were genotyped. Allelic frequencies of these SNPs were 30% or more. WAP8-13 genes were present in one linkage disequilibrium block. Dark black areas represent intense linkage disequilibrium, while white areas represent D'<0.5. FIG. 3(b) shows haplotype blocks and P-value distribution. The haplotype blocks contained 18 common SNPs including WAP12 3' flanking +1264G>A. The most significant association was observed for a plurality of SNPs including WAP12 3' flanking +1264G>A. FIG. 3(b) discloses SEQ ID NOS 22-25, respectively, in order of appearance.

FIG. 4 shows the results of expression and localization analyses. FIG. 4(a): LBP-32 was allowed to be expressed in a human heart tissue, HCASMC, and HCAEC. TSBP was allowed to be expressed in a human heart tissue and HCAEC. FIG. 4(b): TSBP was localized in the cytoplasm of HCASMC. LBP-32 was localized in the nucleus of HCASMC.

SEQUENCE LISTING

Figure 1:
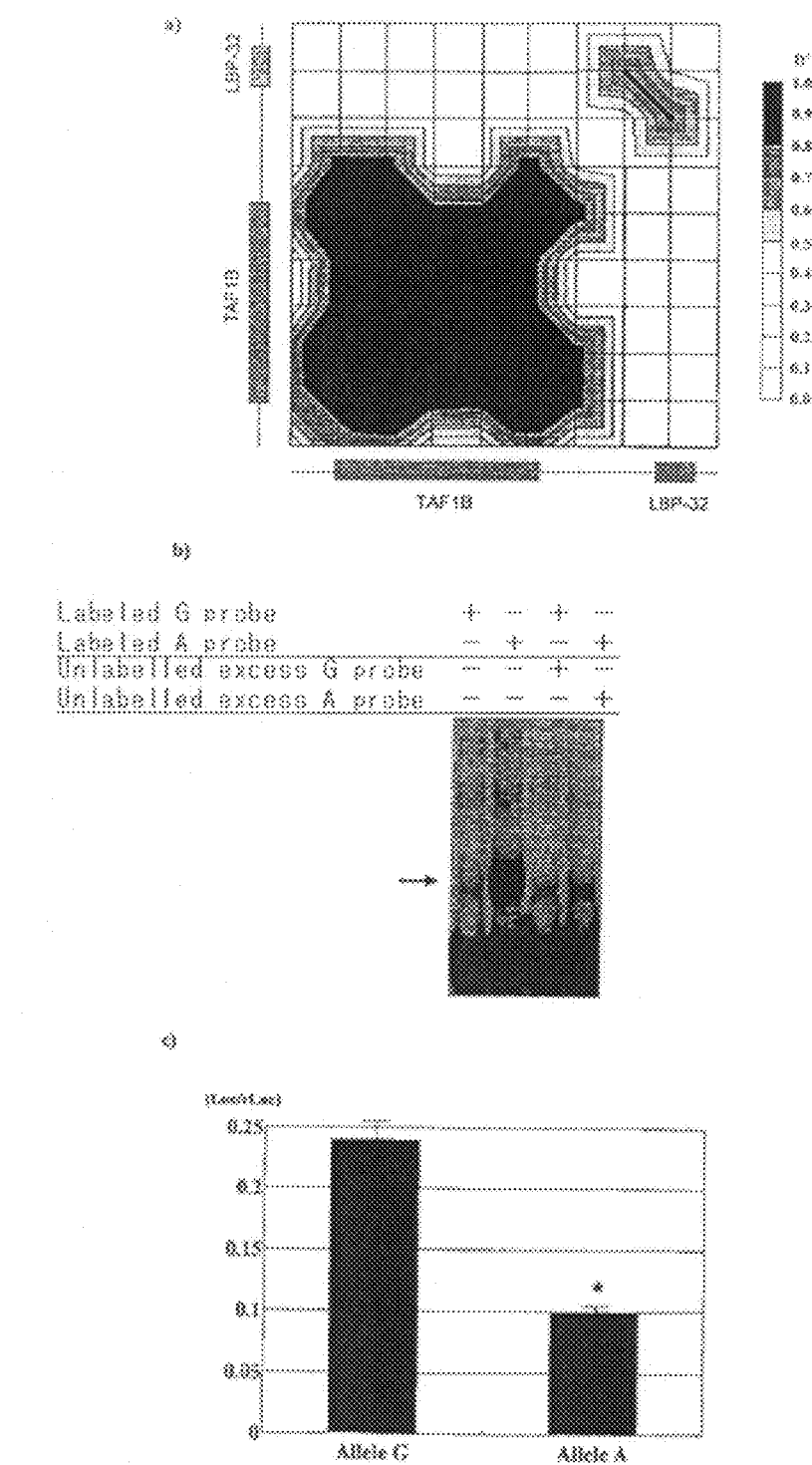
FIG. 1 shows the results for LBP-32.
Figure 2:
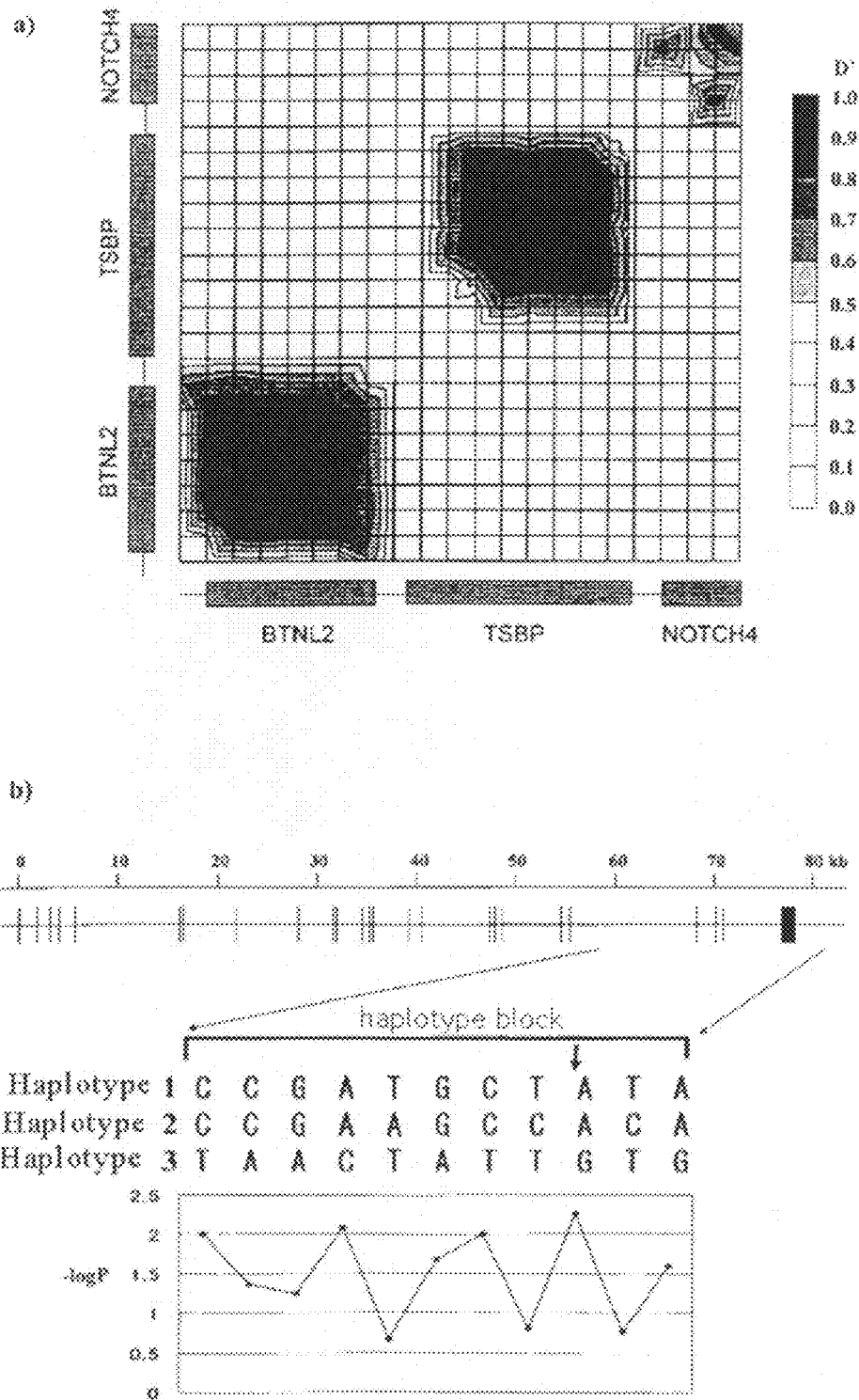
FIG. 2 shows the results for TSBP.
Figure 3:
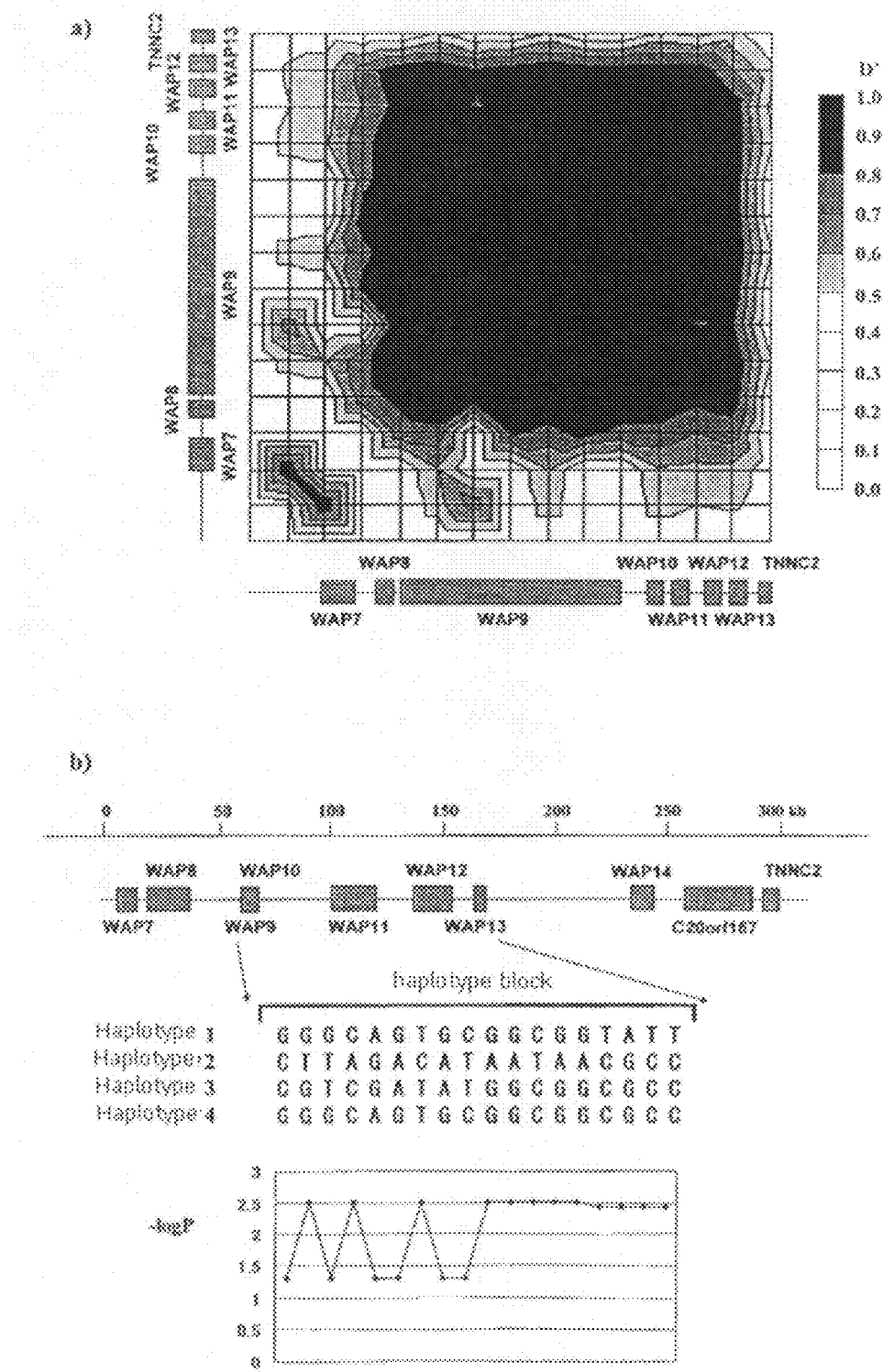
FIG. 3 shows the results for a WAP gene region.

```
<160> NUMBER OF SEQ ID NOS: 25

<210> SEQ ID NO 1
<211> LENGTH: 3061
<212> TYPE: DNA
<213> ORGANISM: Homo sapiens

<400> SEQUENCE: 1
gtgagtgagg cgcaggagtc cggccgccgc gggggggccg cgctgagggg ccgcacctgc      60
agcgagcgag ccgggcgcag acccgaggcc gcgcgggcgg gcgggcgcgg ggcgcgagcc     120
gggggccgct gtccactcca cgccgccacg gcctttgccc cttagccctg ccgtgctctt     180
tgttcggtcg gagcctcggg aggagagacc ctgtcctcgg ggaaactcga caccggaggg     240
gccaccctcc tccctcctc cgcggccagg ttgggtcccc tcgggcgcgc accttggggt      300
ccgggccccc ggcgcggtcg ggtgcggcgc gaggtcgggg cgcagccaac gccccgggc      360 ctccccgccc ccctctcctg cccggtcggc ctcgggagcc tggtggggct cgcgccgcgt     420
cgggacaggt ggacttctcc aggtaatctg tggtctcagg ctcgtcactc ggcgacctgc     480
tggaacctcc aaaacagaaa tgtagggaaa ggttgaagtg ccccgatgtc cgggcgtttt     540
cttttccctg gctggcggca tgagtgggaa aacggctgta ggagttattt tgccacttgc     600
atcattgatg gtaattacag attaccgtgt ttttagtgct cgagagaatc aagaggatga     660
aactttgaaa tccgggtgtt aaacgagaaa gtactgtaca agctaatatg cttttttagag    720 tgtgtgattt aaaagcgtat ttcgacaaat gtgaggtggt agtgtaataa ggcatggggg     780
```

-continued

```
attaactggg cgagggagtt tctgtatttt tctttgcagc ttttctgaaa atataaaatt    840
gtcctaaaaa ttttaaaaac ttactaaaga aaaaacaggg aaatcgcacc aggccagtca    900
gtatatttca gatcaggaag tttaaggcag ataggtaccc ctcccagttt cttagttatt    960
tgtgaaggat cggttttgt cagtgtgttc tttttctgga tgagatagat attttgtatg   1020
gagtatctta aatggattac tcttatgttg tagaatatgc agttaaatta ttgcctgaaa   1080
catatttcag aagtctgaga gatcgcagac gcggagttta aggctcacct gaaagtgatg   1140
atgagccttc ggcgactgaa gcctacttcc tgactgtcat gaggaagtgg actaagaaag   1200
gcaactggtt ttgtgtttat ttcttgacgt atagtttaga taaggcaaat tttccaaagc   1260
taacattttg gccttaggca ggctttggaa atatgaaaca ccttcagggt gattccaaac   1320
ataaagccat ttcttctct gttttctatt gcttgtacaa atttgggatg tgggtgggag   1380
aagaagggaa gttgaaaact agcattaagg gaattgaaca gccaagtgct gtcatagtct   1440
tctggaagta gctattacgc tattaattat agcttagcag tacatcagtc aatcagtcca   1500
tggcaccagc cgttcagtag ctgttgtact ctggtcctga tggctcaggg aatgccactt   1560
tgtatatttc tttatttct ttaaagttga gatttgtgta agcaatcttc tccattttta   1620
gacaaatgat ctgctggctt tgaacagtct tttatgtttg ttttgtgtta aaatagtata   1680
ccacctcaag actttcttac caaatgtaac gtttatgcca aaacgtgagt aaaaacattg   1740
gctttcaaat aacacttcat tttgactgag gatacattgt tggatttttt tccccttttt   1800
tgaagatgtt ctccttttc taaatctgta tctgttctta aaggccctgg gtgactccca   1860
aacgctaacc tttgttgatt acttgaaaag ataatcagtc tttctacatt cacttttaaa   1920
ataggcaggt cacctttagg ccatttacat atttcatttg tgtgttgcaa tgagagccag   1980
tccttcaatt tgcttgttag aattgtaata attcagagga gttccaaaca tttaaaattt   2040 attttttctcc ttgaaaataa actgctttgt tttgctagag tcagtgttcc attttttctc   2100
tttattgact tattaaatag taccaaccga acagttgttg agactgttta catttcaagt   2160
ttttggaatt agtaatgttt gctttaatct tttaaattaa atcttctgta aggtttcact   2220
aagatcgcca ttgattttt tggatttttc ccaccaaact acagtgttaa aatgaaacag   2280
ttcttgtgca atgtggaaaa ctagcaaaga tttttttaaaa gccagatttt cccacctatt   2340
ttttttaaaa cttttttgttc agtggcttca tttattgttg gatatcctta agtgtttatc   2400
tctaagataa acagttaact cccatgccag aaaattatgc ctctttattg atttacagtc   2460 cccctttggcc acattccatg ctcaatctgc tggtaatcag tagaatattc tggctttctc   2520
atatcccctg gaggattgcg tgaaggatcc cttttttctt ctgctgcttc tcccctcccc   2580
actgtgttca ggtaggaatt tttaaggcat ggcagccaca gtagaaagag ggaataacat   2640
gtagcagtgt gatgaacggc acacgctctt ctcaagaggg gacagtcctg attgtgtgtt   2700
ggaagagaac aagtattctc ttttctttac tgtgtccttg tgtttgttta tggaaagtat   2760
ttgaatagcc tggcatttc tcggggatgg ttttgtttcg cttttttgcc aaatagtata   2820
ccctgggttc cacgtgtagg tgaactgcca gttctctggc tgcctagata ctttatgtct   2880
tactgtggga cccattggtc tgcacttacg tggtttgtct tctggtcttg tcttaatttg   2940
acttcctagg gtcattgatg aaacaatagg ctatttata ggaatgtcaa ggaattggta   3000
gcttatgata ccttgcagta gaaaagtgtg tgttttgtt ttttttttaa tttctctgaa   3060
g                                                                  3061
```

<210> SEQ ID NO 2
<211> LENGTH: 1055
<212> TYPE: DNA
<213> ORGANISM: Homo sapiens

<400> SEQUENCE: 2

| | |
|---|---|
| ttatattaac aggttacatg gatgaagaac ttgcaaaaaa accttgttcc aaaatccaga | 60 |
| ttctaaaatg tggaggcact gcaaggtctc agaatagccg agaagaaaac aaggaagcac | 120 |
| taaagaatga catcatattt acgaattctg tagaatcctt gaaatcagca cacataaagg | 180 |
| agccagaaag agaaggaaaa ggcactgatt tagagaaaga caaatagga atggaggtca | 240 |
| aggtagacag tgacgctgga ataccaaaaa gacaggaaac ccaactaaaa atcagtgaga | 300 |
| tgagtatacc acaaggacag ggagcccaaa taaagaaaag tgtgtcagat gtaccaagag | 360 |
| gacaggagtc ccaagtaaag aagagtgagt caggtgtccc aaaaggacaa gaagcccaag | 420 |
| taacgaagag tgggttggtt gtactgaaag gacaggaagc ccaggtagag aagagtgaga | 480 |
| tgggtgtgcc aagaagacag gaatcccaag taaagaagag tcagtctggt gtctcaaagg | 540 |
| gacaggaagc ccaggtaaag aagagggagt cagttgtact gaaaggacag gaagcccagg | 600 |
| tagagaagag tgagttgaag gtaccaaaag gacaagaagg ccaagtagag aagactgagg | 660 |
| cagatgtgcc aaaggaacaa gaggtccaag aaaagaagag tgaggcaggt gtactgaaag | 720 |
| gaccagaatc ccaagtaaag aacactgagg tgagtgtacc agaaacactg gaatcccaag | 780 |
| taaagagag tgagtcaggt gtactaaaag gacaggaagc ccaagaaaag aaggagagtt | 840 |
| ttgaggataa aggaaataat gataaagaaa aggagagaga tgcagagaaa gatccaaata | 900 |
| aaaaagaaaa aggtgacaaa aacacaaaag gtgacaaagg aaaggacaaa gttaaaggaa | 960 |
| agagagaatc agaaatcaat ggtgaaaaat caaaaggctc gaaagggcg aaggcaaata | 1020 |
| caggaaggaa gtacaacaaa aaagtggaag agtaa | 1055 |

<210> SEQ ID NO 3
<211> LENGTH: 1284
<212> TYPE: DNA
<213> ORGANISM: Homo sapiens

<400> SEQUENCE: 3

| | |
|---|---|
| gatcctgcct cttttgctgc cactacaggt gatcattgag agcccactgt agcccccaaa | 60 |
| gatgccccac tcatcttgtg tcctggtgtt tgatttctct ccctggctat gcttctctac | 120 |
| cctccttctc cttctttggc ccatgtatcc ctcccagccc tcaggatgcc cagccccttg | 180 |
| ctgttttgct cactgaacca gtactcccag ggggaggaac tgctcatgtg cagcgtctcc | 240 |
| tgatgctaag gagaacattt ctcaccctgg agtcagaagg acccattaag cacgagatgg | 300 |
| gtggcagtta gaacccaagg taaagagtgg gaggccccca agcactgctt tggtctcctt | 360 |
| agccttggta ctcccccacc tcatgctccc caatctcttt ctgagcttca gattgctgtc | 420 |
| tctttacaat gaggataatg agtcccagga aggccagcga catgcctaag gccacaagag | 480 |
| agagagagga tatgatgtgg ccggaagagg atgtttcctc tgagctcact ttttctcact | 540 |
| tctctccatt acttgagacc agaggcatcc tagtgagagt gagtgcctgc accaaccca | 600 |
| aagctcctcc tatccagcac ccaccaacat ggctactcct ctgatgggac ccaatttggg | 660 |
| tctcaggatc taacactcca gcaccttcca ttaactgaat agtccctatc tttcccaagc | 720 |
| cctcttcctt agaggcttat tctctttct tttgatcaag aggaacacca aggggtgggg | 780 |
| aacaggtggt tcatgctgct attgctaagg agtaattggc acagagtggc agtgggtctt | 840 |

```
gcctgtcatc ctactgtgag ttagtggaaa ttaaccactg tggtacagac tctcccttac    900
tctatgcaat cgcaactcct ctgaaatgat cctggggcca gatccagggt tgcatcacat    960
gtggctaatt ggaacacgga gtcaaatgtg aagaggtttc aggaggacag gccatgccca   1020
gaggcaggtg tgcagtgtta tgctccagtc tagtgcttct tgctgggcta ttcaatgaaa   1080
gagacatcag agaagaaaac ttcccccatc agaccagagg ccatgagcca cctctgaggc   1140
atcacaccag gctctggata tctcagattt gtcttcacct ttctcaagag cttttcttgg   1200
acaagggagt cttagaaaag agatcataat caactaccaa cacagacatc atcagcagta   1260
ggtgggctat aagggcatgg tctc                                          1284
```

```
<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 4
tccacgccgc cacggccttt gcccctta                                        28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 5
tccacgccgc cacgaccttt gcccctta                                        28

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 6
actttggctg tcatcctgac                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 7
cttgataggt cctgtagctc                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 8
```
agcgcgatga cacaggagta                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 9
cgttgctatg gagacagtga                                              20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 10
tggtatcgtg gaaggactca t                                            21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 11
gtgggtgtcg ctgttgaagt c                                            21

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 12
atagcggccg caatgacagt cttggaaata ac                                32

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 13
agactcgagt tactcttcca cttttttgtt gtac                              34

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 14
gaggcggccg cgatgacaca ggagtacgac aac                               33

```
<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 15
agagtcgacg atctccgtca gggtgagc                                          28

<210> SEQ ID NO 16
<211> LENGTH: 41
<212> TYPE: DNA
<213> ORGANISM: Homo sapiens

<400> SEQUENCE: 16
taaaaatcag tgagatgagt rtaccacaag gacagggagc c                            41

<210> SEQ ID NO 17
<211> LENGTH: 41
<212> TYPE: DNA
<213> ORGANISM: Homo sapiens

<400> SEQUENCE: 17
gtccactcca cgccgccacg rcctttgccc cttagccctg c                            41

<210> SEQ ID NO 18
<211> LENGTH: 41
<212> TYPE: DNA
<213> ORGANISM: Homo sapiens

<400> SEQUENCE: 18
agacatcatc agcagtaggt rggctataag ggcatggtct c                            41

<210> SEQ ID NO 19
<211> LENGTH: 11
<212> TYPE: DNA
<213> ORGANISM: Homo sapiens

<400> SEQUENCE: 19
ccgatgctat a                                                            11

<210> SEQ ID NO 20
<211> LENGTH: 11
<212> TYPE: DNA
<213> ORGANISM: Homo sapiens

<400> SEQUENCE: 20
ccgaagccac a                                                            11

<210> SEQ ID NO 21
<211> LENGTH: 11
<212> TYPE: DNA
<213> ORGANISM: Homo sapiens

<400> SEQUENCE: 21
taactattgt g                                                            11

<210> SEQ ID NO 22
<211> LENGTH: 18
<212> TYPE: DNA
<213> ORGANISM: Homo sapiens

<400> SEQUENCE: 22
```

```
gggcagtgcg gcggtatt                                              18

<210> SEQ ID NO 23
<211> LENGTH: 18
<212> TYPE: DNA
<213> ORGANISM: Homo sapiens

<400> SEQUENCE: 23
cttagacata ataacgcc                                              18

<210> SEQ ID NO 24
<211> LENGTH: 18
<212> TYPE: DNA
<213> ORGANISM: Homo sapiens

<400> SEQUENCE: 24
cgtcgatatg gcggcgcc                                              18

<210> SEQ ID NO 25
<211> LENGTH: 18
<212> TYPE: DNA
<213> ORGANISM: Homo sapiens

<400> SEQUENCE: 25
gggcagtgcg gcggcgcc                                              18
```

The invention claimed is:

1. A method for detecting genetic polymorphisms existing in the LBP-32 gene, the TSBP gene, and the WAP12 gene which comprises:

obtaining a biological sample containing an LBP-32 gene sequence, a TSBP gene sequence, and a 3' flanking region of a WAP12 gene sequence from a subject; and assaying for the presence of a group of single nucleotide polymorphisms consisting of an A or G at position 151 in intron 1 of the LBP-32 gene;
an A or G at position 306 of exon 25 of the TSBP gene; and
an A or G at nucleotide 1264 in the 3' flanking region of the WAP12 gene.

* * * * *